United States Patent [19]

Landau

[11] Patent Number: 4,966,581

[45] Date of Patent: Oct. 30, 1990

[54] NON REUSABLE DISPOSABLE CAPSULE CONTAINING AN INDIVIDUAL VACCINE DOSE TO BE HYPODERMICALLY INJECTED WITH A PRESSURE NEEDLELESS INJECTION APPARATUS

[75] Inventor: Sergio Landau, Rio de Janeiro, Brazil

[73] Assignee: Vitajet Industria E. Commercio Ltda, Rio de Janeiro, Brazil

[21] Appl. No.: 229,566

[22] Filed: Aug. 5, 1988

[30] Foreign Application Priority Data

Apr. 22, 1988 [BR] Brazil ........................ PI18801952[U]

[51] Int. Cl.⁵ .............................................. A61M 5/30
[52] U.S. Cl. ...................................... 604/72; 604/244
[58] Field of Search ................... 604/72, 68, 415, 148, 604/244, 218; 215/32

[56] References Cited

U.S. PATENT DOCUMENTS

| | | | |
|---|---|---|---|
| 2,687,730 | 8/1954 | Hein, Jr. ................................. | 604/72 |
| 3,945,383 | 3/1976 | Bennett et al. ........................ | 604/72 |
| 4,747,501 | 5/1988 | Greaves ................................. | 215/32 |

Primary Examiner—Stephen C. Pellegrino
Attorney, Agent, or Firm—Ladas & Parry

[57] ABSTRACT

This invention related to a simple device for hypodermic pressure-injection which does not make use of needles for introducing the vaccine into the patient's body, and which is fully constituted by low cost disposable material self-destroying after being utilized a single time. This device already contains within it, a single metered dose of vaccine or medication to be injected and, when in use, it comprises solely four elements; and injector nozzle with an outlet orifice, a sealing disc, a cylindrical body and the dose itself of vaccine to be injected. The device, referred to as disposable capsule, is used at the front portion of a pressure-injection apparatus and aims at establishing a vaccination means which is simultaneously disposable, fast, safe, of low operational cost and mainly that does not make use of hypodermic needles and whose assembly which touches the patient at the injection site is self-destroyed after a single use, thereby avoiding any possibility of reuse and consequent possibility of disseminating blood-transmittable diseases.

16 Claims, 6 Drawing Sheets

NON REUSABLE DISPOSABLE CAPSULE CONTAINING AN INDIVIDUAL VACCINE DOSE TO BE HYPODERMICALLY INJECTED WITH A PRESSURE NEEDLELESS INJECTION APPARATUS

BACKGROUND OF THE INVENTION

This invention relates to a capsule made of disposable material containing a vaccine or medication dose to be hypodermically injected into the bodies of persons or animals through the use of a pressure injection apparatus. Once the capsule is put into use and the amount of liquid within the same is injected into the patient, the capsule is rendered useless so as to avoid reuse thereof, as in the case of the usual disposable syringes. Besides the fact that this capsule is previously filled with the correct dose of liquid to be injected, the major difference between it and the known means of hypodermic injection resides in that, in the case of the present invention, there is no needle to introduce said liquid through the skin. At the front portion of the capsule, there is only a very small orifice through which the liquid passes as a high velocity jet penetrating into the intradermic, subcutaneous or intramuscular tissues depending on the injector pressure. The major difference between the other pressure injector means and the present invention is that, in the present case, all the parts in contact with the medication are necessarily disposable after every application, since all these parts are contained within the capsule itself, which is self-destructive after use. In this sense, the only part which contacts patient's hypodermis at the injection location, that is, the nozzle itself with the orifice, is also an integral part of the capsule and therefore it is necessarily disposable after a single use. This definitively prevents any possibility of contamination from one patient to another, since every person would be necessarily vaccined with a new sterile nozzle.

Pre-sterilized disposable syringes are utilized worldwide in large scale and the practicability and safety thereof have been demonstrated for more than twenty years. However, disposable syringes and needles are often utilized twice or more by persons who aim at a great economy and utility of the product. For instance, this is the case of diabetic people who must take hypodermic injections daily and, not rarely, they use the same syringe and needle three times or more. Eventually, these persons put the disposable material into boiling water between use, since these materials are capable of sustaining one or two rapid contacts with boiling water. Reuse of disposable syringes, in this case, does not provide for the initial safety and sterility as guaranteed by the manufacturer in the tamper-proof package.

Nevertheless, this is not the major problem with disposable syringes since when they are used more than once by the same person, the hazards of infection are not too great, since contamination can only result from external media. Since there is an increasing diffusion of the use of injectable hallucinogenic drugs in our society, used disposable syringes came to be very sought after by drug consumers and frequently the same hypodermic needle is used many times by several persons without effecting intermediate asepsis. The hypodermic needle comes into direct contact with many individuals, therefore it is one of the most efficient ways of transmitting virus and bacteria from one person to another. In this way, cases of dissemination of blood-transmittable diseases, such as AIDS, have recently considerably increased by virtue of this reuse of disposable syringes and needles by drug users. This is now the most important problem in connection with these articles.

Since the past decade, this problem, has begun to be reflected by the inventions which have been developed aiming at improving the hypodermic injection methods or means that make use of disposable materials. Special attention has been drawn to ideas which suggested self-destruction after the first use. As typical examples of these ideas, one may cite the following patents: YERMAN (U.S. Pat. No. 4,233,975); CHIQUIAR (U.S. Pat. No. 3,998,224) and STAEMPFLI (U.S. Pat. No. 4,391,272). All these teachings disclose in one way or another the destruction of the syringe after use. On the other hand, however, these patents suggest a product which is more sophisticated and costly rather than inexpensible by virtue of being disposable. For this reason, practical commercial applications thereof have been quite limited.

Ideas have been developed for simple syringes without a movable piston and already containing therewithin the exact dose of medication to be injected. As typical examples, one may cite the following patents: CUNNINGHAM (U.S. Pat. No. 4,013,073) and MCALLER (U.S. Pat. No. 4,018,222). By utilizing these inventions, it would be enough to cause the needle to penetrate into the hypodermis and to squeeze with the fingers the medication flexible container. In this way, all the liquid would penetrate into patient's body through the needle and it is supposed that such container and needle would not be used again. However, even this type of syringe pre-filled with an individual dose may be reused. Although, at the expense of more labor than for the usual disposable syringes, refilling thereof can be done through the needle itself by suction from another container holding some other drug. Consequently, reuse of these products is possible.

On the other hand, the method of needleless pressure injection is also largely known and it has been employed in many countries for the last three decades. This method consists basically of putting a minute orifice in contact with a patient's skin so that a dose of medication is delivered through the orifice into the hypodermis under high velocity. Liquid is propelled against said outlet orifice by a piston generally actuated by a mechanism which biases and then releases a high compression spring. These hypodermic pressure injectors have been designed to render hypodermic injection more comfortable and to speed up the procedure of preparation and application thereof.

These injectors have been made simpler over time and presently they are used even individually by diabetic people to apply their own daily insuline dose. As a typical example of this situation, I can cite my own patent, LANDAU (U.S. Pat. No. 4,592,742).

However, recently, with the use of these hypodermic injectors in general public, suspicions have arisen that they also can disseminate transmittable diseases through blood. This suspicion derives from the fact that, upon receiving the liquid jet, a blood droplet can arise immediately at the site of application and this blood droplet could contaminate the orifice of the injector nozzle. This situation limits the utilization of pressure injectors for vaccination.

Therefore, it is understood that the only absolutely safe manner of avoiding blood contamination as caused by pressure injectors in vaccination campaigns would be that of using one new nozzle with the associated outlet orifice for every single person to be vaccined. That is, the nozzle with outlet orifice would be disposable and would have to be necessarily replaced after each application.

SUMMARY OF THE INVENTION

The present invention aims exactly at disclosing a hypodermic injection device which, upon being utilized by a small group of persons or by a crowd such as in the case of mass vaccination, does not allow for any possibility of disseminating blood transmittable diseases. This is the basic goal of the invention.

Further criteria that the present invention seeks to meet are: (a) low cost for the product; (b) simplicity of use; (c) speed throughout the injection procedure; (d) safety in operation; and (e) elimination of the trauma of pricking (which is a very important criterion for children).

All these criteria are observed as a function of the basic characteristics of the present invention. That is: (a) the capsule made of disposable material produced at a lost cost; (b) the preparation of an injection easy since the capsule simply inserted into the injector nose (as described hereinafter); (c) the injection procedure is also very fast, since the preparation is simple and the application itself is completed in less than one second; and (d) the pressure injection method is safe and has been used for nearly thirty years. Also, the incidence of adverse cutaneous reactions is very low. The injector used in the present invention is simply a device which biasses a spring actuating a piston. There is no sealing point in this injector wherein leakages are liable to occur. The only two sealing points of the whole system are a part of the capsule and there is no possibility of damage to the capsule during injection; the essential characteristic of the pressure injection method is exactly the absence of any hypodermic needle and then the absence of trauma of pricking. When the orifice is placed in contact with the skin, only the liquid penetrates into this skin and nothing more.

BRIEF DESCRIPTION OF THE DRAWINGS

The principle and operation of the invention will be disclosed together with the attached drawings, in which.

DESCRIPTION OF THE PREFERRED EMBODIMENT

Figure 1:
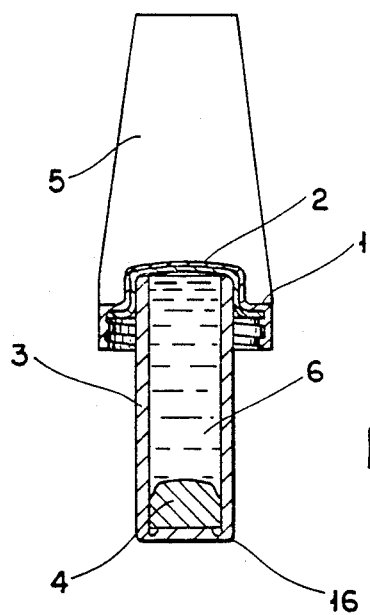
FIG. 1 is a cross-sectional view of all parts which form said capsule.

FIG. 1 shows in cross section the preferred embodiment for the non-reusable, disposable capsule, already containing in its interior, a single dose of vaccine to be pressure injected in the absence of a hypodermic needle. This capsule is composed of four essential elements; a nozzle (1) containing a centrally disposed minute orifice (2) which should be made preferably of a high resistance thermoplastic not presenting any type of oxidation or chemical reaction when is prolonged contact with several types of medications which are to be introduced into the capsule; the so-called capsule body (3) which is preferably cylindrically-shaped and is constituted by a usual thermoplastic material such as polyethylene or polypropylene; a sealing disc (4) preferably formed of some rubber compound suitable for medical use such as, for example, silicone or ethylene-propylene and which will serve to propel the whole liquid dose within the capsule body (3) towards the outlet orifice (2); and finally the vaccine or medication (6) to be injected which will be fully contained and sealed within the capsule. Moreover, nozzle (1) may be frictionally attached or snap-fitted to capsule body (3) so that the nozzle is securely held in place. In addition, there is another accessory element, that is, a protective cover (5) for the nozzle which is removed prior to use of said capsule constituted by usual thermoplastic material and the purpose of which is to seal the nozzle orifice (2) when said capsule is not in use. For protection and for assuring sterility, said product should be sealed within a sterile and tamper-proof package similar to those which are used for the usual disposable syringes.

All the parts constituting said capsule are readily manufactured by commonly known and relatively usual industrial processes. Said parts will be then industrially cleaned and sterilized and the final assembly, the filling of the capsule and packaging are effected in a standard sterile environment, suitable for packaging vaccines and other injectable products. Finally, the already packaged product undergoes an ultimate sterilization process similar to that of ordinary disposable syringes.

Figure 2:
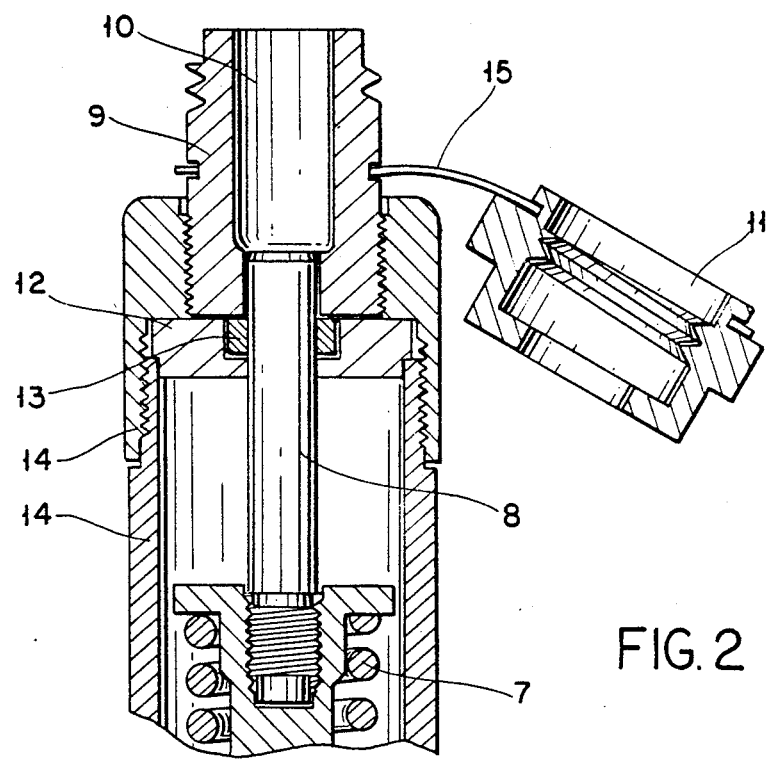
FIG. 2 is a cross-sectional view of the front portion of said pressure injector wherein said capsule is to be used.

In order to empty the capsule and to inject the dose of vaccine into patient's hypodermis, it is necessary to use a device keeping the capsule firmly retained and propel the liquid (6) towards the outlet orifice (2) through a piston or plunger. To this end, use is made of a simple pressure injector mechanism such as, for example, that of my patent LANDAU U.S. Pat. No. 4,592,742. This mechanism comprises: a spring (7), a piston (8); a cylinder (9) having therewithin a space (10) which is also cylindrical and wherein said disposable capsule will be housed; a capsule-retaining cap (11) which will serve for fixing and retaining the capsule into the cylinder (9) during injection; centering and guiding means (12) and (13) which will serve for keeping piston (8) concentrically arranged in relation to the cylinder (9) throughout the travel thereof; and an external body (14) also formed by concentric elements. The system for backward movement of piston (8) and compression and bias of spring (7) is part of the injector mechanism and is widely disclosed in my patent LANDAU U.S. Pat. No. 4,592,742. In FIG. 2, piston (8) is shown already recoiled and ready for being actuated, that is, spring (7) is already compressed.

Figure 3:
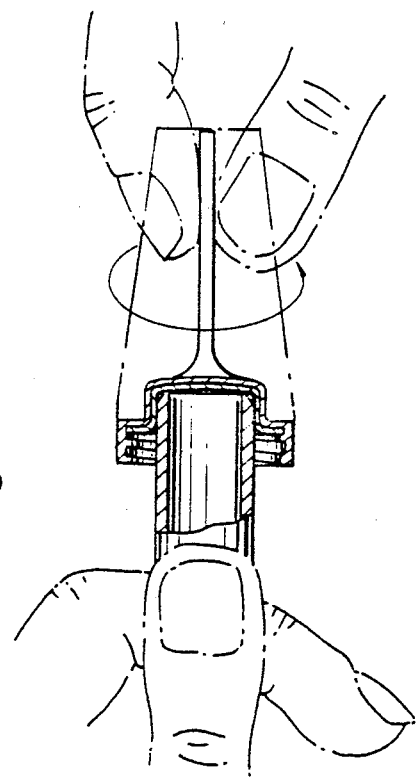
FIG. 3 is a partial cross-sectional view at the moment wherein the cap of the nozzle is being removed from the capsule.
Figure 3A:
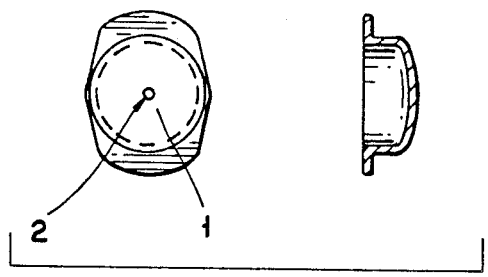
FIG. 3A represents two plan views of the capsule nozzle alone containing the outlet orifice.

The complete capsule, as shown in FIG. 1, will maintain the sterility even if it is removed from the tamper-proof package since the vaccine is sealed therewithin, at the rear end, by sealing disc (4) and, at the front end, by nozzle cover (5) which will seal outlet orifice (2). Nozzle cover (5) operates exactly as the needle covers in ordinary disposable syringes, that is, it should be removed at the moment of injection. It is also secured in the same manner as in the usual syringes. The projecting lips of nozzle (1), as shown in detail in FIG. 3A, are employed for securing cover (5) against nozzle (1) through an internal helical screw thread existing at cover (5) mouth. In order to remove such a cover (5), it is enough to cause it to rotate, as shown in FIG. 3. It should be noted that other conventional closure means can be also be used to secure the cover to the nozzle.

Once cover (5) has been removed, the capsule is ready to be inserted into the injector.

Figure 4:
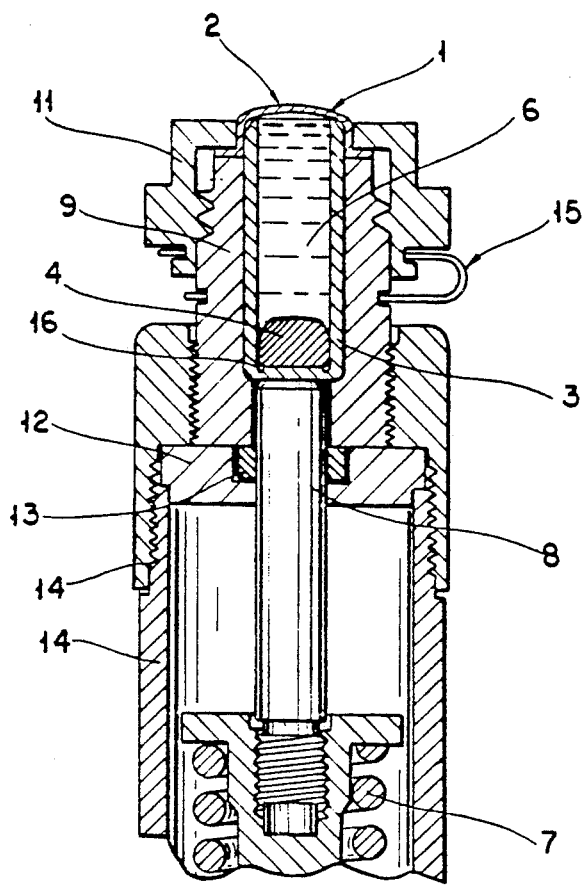
FIG. 4 is a cross-sectional view of the front portion of the pressure injector already containing a ready-to-apply capsule.

FIG. 4 show the capsule already housed within the injector cylinder (9). Capsule-securing cap (11) is already screwed into the cylinder (9) through a quick-tightening screw thread. Cap (11) will prevent the capsule from moving forward during travel of piston (8). Said cap (11) is permanently secured to the cylinder (9) by means of a strip (15) of flexible material serving to remind the vaccinator that cap (11) should be replaced after each injection. FIG. 4 shows therefore the system ready for injecting the vaccine into hypodermis, that is, spring (7) is compressed, piston (8) is recoiled, capsule is housed in cylinder (9) and cap (11) is screwed on.

Figure 5:
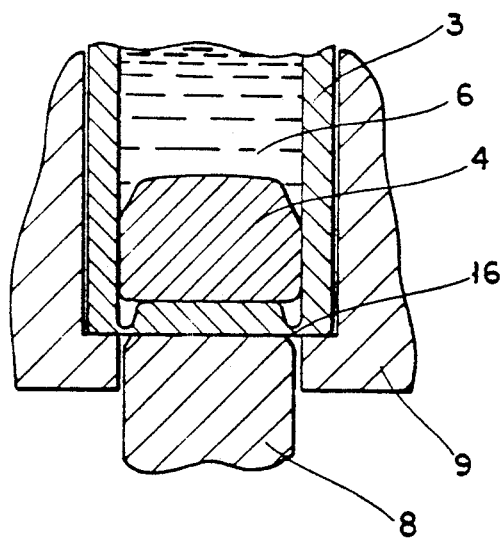
FIG. 5 shows a detail of the rear portion of the capsule wherein, at the beginning of injection, rupture of said capsule takes place.
Figure 6:
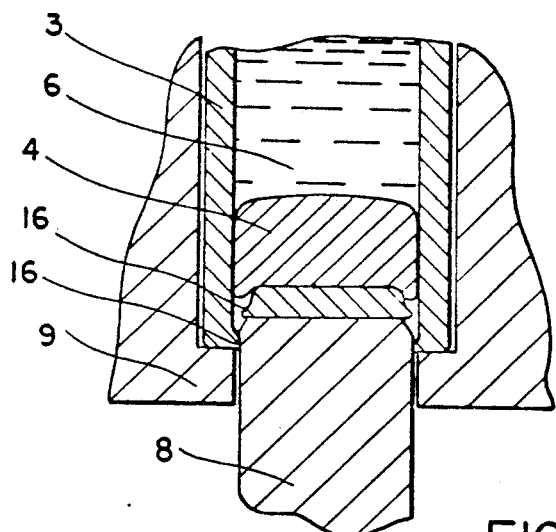
FIG. 6 shows a detail of the rear portion of the capsule just after rupture thereof has occurred.

Self-destruction of capsule is caused at the exact moment in which the so-called injection is initiated. Through FIGS. 5 and 6, it is well understood how this self-destruction procedure is carried out. Capsule body (3) has a wall of constant thickness material along the entire length thereof. There is a single exception for the joining circular flange (16) between the bottom and the cylindrical portion of the body. In this circular flange, the thickness of the wall of material is about ¼ of the thickness of the rest of the piece. When the injector is actuated, piston (8) is quickly moved forward by the action of spring (7). Therefore, piston (8) itself plays the role of destroying capsule by detaching the bottom thereof, through the instantaneous rupture of circular flange (16). The postrupture instant is represented in detail in FIG. 6.

Figure 7:
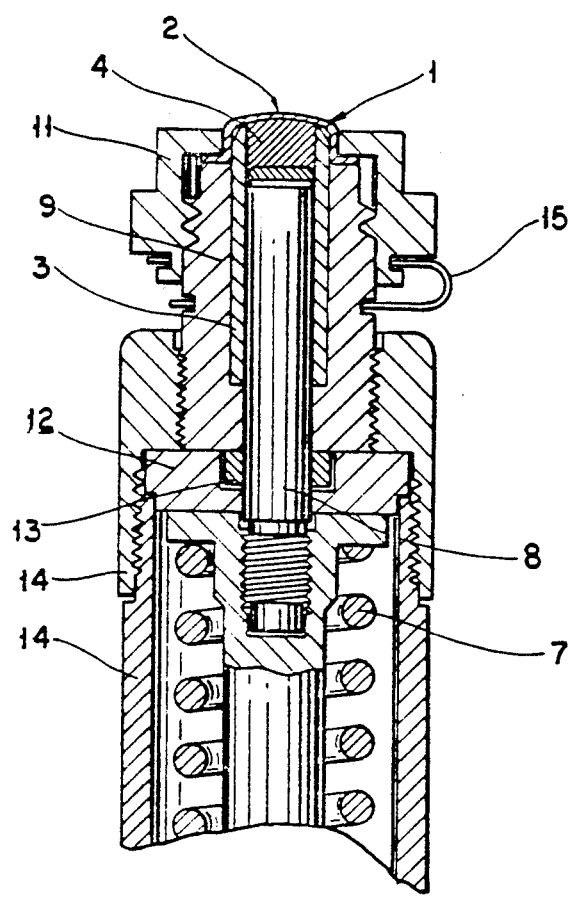
FIG. 7 is a cross section of the front portion of the pressure injector containing the already empty and destroyed capsule, after injection is complete.

FIG. 7 shows the whole assembly after injection is completed. It is to be noted that spring (7) is discompressed, piston (8) is all projected forward, capsule body bottom and sealing disc (4) are at the front end of the capsule and are located across nozzle (1). The capsule of course is empty since the vaccine which was contained in its interior has been fully expelled by the sealing disc (4) through outlet orifice (2).

Figure 8:
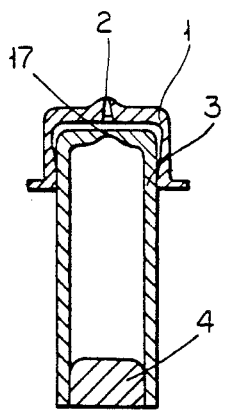
FIG. 8 is a cross-sectional view of an additional embodiment of the capsule.
Figure 10:
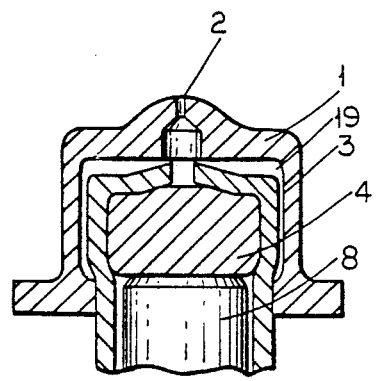
FIG. 10 is a cross-sectional view of the capsule of FIG. 9 after the body of the capsule has been ruptured.
Figure 9:
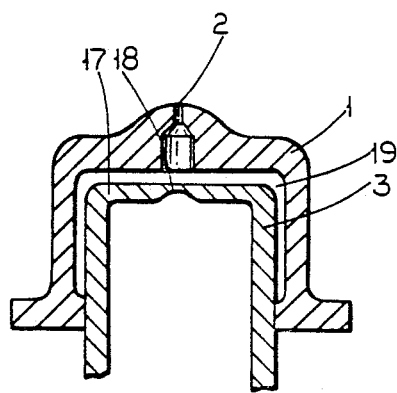
FIG. 9 is an enlarged view of the top portion of the capsule shown in FIG. 8.

FIGS. 8-10 show an additional embodiment of the capsule with a body (3) having a closed front end and an open rear end. Inserted into that rear end is sealing disc 4 which is moveable within body (3). Moreover, a top wall (17) of the body has a weakened portion that can be ruptured.

As can be seen in FIGS. 9 and 10, an upper portion of nozzle (1) is spaced apart from the front end of the body (3) so as to form gap (19). When sealing disc (4) is engaged by piston (8) and moved towards the front end, weakened portion (18) ruptures and the fluid inside the body is ejected through orifice (2).

After the ejection stroke has been completed, sealing disc 4 pushes the body outward into gap (19) so that the nozzle and body become locked as shown in FIG. 10. As a result, the capsule cannot be reused.

To introduce the liquid to be injected into the capsule, a hypodermic needle can be inserted through sealing disc (4) into the cavity formed by body (3). When the needle is removed, the self-sealing nature of sealing disc (4) closes the hole made by the needle.

In brief, the whole process of hypodermic injection in accordance with the present invention comprises the steps of: (a) preparing the injector through compression of the spring (7) and consequently recoil of piston (8); (b) removing the capsule from the package; (c) removing the nozzle cover (5) from the capsule; (d) inserting said capsule into the injector cylinder (9); (e) screwing on the capsule-securing cap (11), (f) placing nozzle (1) in contact with patient's (g) firing said injector; (h) unscrewing the securing cap (11); i) removing the already destroyed capsule from the cylinder (9) and disposing it.

What is claimed:

1. A disposable capsule for a needleless hypodermic injection device comprising:
    a hollow body having an open front end and a rear end that is closed by a bottom wall that is attached to the body by an outwardly extending flange having a smaller thickness than a remaining portion of the bottom wall, said body is connectable to said hypodermic injection device so that a piston can engage the bottom wall and detach said flange from said body;
    a nozzle, attached to the front end of the body, having a minute front orifice through which a liquid to be injected can expelled in the form of a jet; and
    a sealing disc within said body so as to prevent the liquid within the body from leaking out the rear end, said disc is moveable from a first position at the rear end of the body to a second position at the front end of the body so that the liquid to be injected can be expelled out said orifice, said disc immediately moves when said piston detaches the flange and moves the bottom wall toward the front end.

2. The disposable capsule according to claim 1, wherein a removable cover is connected to said nozzle so as seal the orifice and wherein said nozzle is made of a high resistance thermoplastic such as polycarbonate or polyacetal, said body and cover are made of such thermoplastic material as polythylene or polypropylene, and the sealing disc is of molded from a rubber compound such as silicone or ethylenepropylene.

3. The disposable capsule according to claim 2, wherein at the bottom wall has a small centrally-located orifice to permit the air to be expelled off when said sealing disc is being introduced into said body and can allow a hypodermic needle to pass through said bottom wall and said disc so that the fluid to be injected can be placed within the body.

4. The disposable capsule according to claim 3, wherein the nozzle is snap-fitted to the open front end of body so that any attempt of separating the nozzle and the body will cause said body to be plastically deformed preventing it from being reused in the injector device.

5. The disposable capsule according to claim 2, wherein both the nozzle and body are cylindrical, and wherein the cover is firmly fitted to the nozzle by a double-entry helical screw thread located inside a circular end of said cover so that two diametrically-opposed lips of said nozzle can penetrate in between the two threads of said helical screw until a bottom portion of the cover abuts and seals the orifice.

6. The disposable capsule according to claim 5, wherein the cover contains the inscription of the type of vaccine, number of the lot and date of manufacture, so that even after the cover is removed from the individual package, the capsule can be identified as to the contents thereof.

7. The disposable capsule according to claim 6, wherein identification of the capsule contents is assisted by the change of colors of the thermoplastic material used for molding the body since each type of vaccine corresponding to a different color.

8. A disposable capsule, for a needleless hypodermic injection device, comprising:
   a hollow body having a front end closed by a top wall, and a open rear end said top wall is attached to the body and has a center portion having a smaller thickness than the remaining portion of the top wall so that it can be easily ruptured, and said body is connectable to said hypodermic injection device so that a piston in the injection device can move within the body;
   a nozzle, attached to the front end of the body, having a minute front orifice through which a liquid to be injected can be expelled in the form of a jet; and
   a sealing disc positioned within the body at the rear end so as to prevent a liquid within the body from leaking out the rear end, said disc is moveable from a first position at the rear end of the body to a second position at the front end of the body so that the top wall can be ruptured and the liquid to be injected expelled out said orifice, said disc moves when engaged by the piston as the piston moves through the body towards the front end.

9. The disposable capsule according to claim 8, wherein a removable cover is connected to said nozzle so as seal the orifice and wherein said nozzle is made of a high resistance thermoplastic such as polycarbonate or polyacetal, said body and cover a made of thermoplastic materials such as polyethylene or polypropylene, and the sealing disc is molded from a rubber compound such as silicone or ethylene-propylene.

10. The disposable capsule according to claim 9, wherein both the nozzle and body are cylindrical, and wherein the cover is firmly fitted to nozzle by a double-entry helical screw thread located inside a circular end of said cover so that two diametrically-opposed lips of said nozzle can penetrate in between the two threads of said helical screw until a bottom portion of the cover abuts and seals the orifice.

11. The disposable capsule according to claim 10, wherein the cover contains the inscription of the type of vaccine, number of the lot and ate of manufacture, so that even after it is removed from the individual package, the capsule can be identified as to the contents thereof.

12. The disposable capsule according to claim 11, wherein identification of the capsule contents is assisted by the change of colors of the thermoplastic material used for molding the body since each type of vaccine corresponding to a different color.

13. A disposable capsule according to claim 8, wherein a lower portion of the nozzle is attached to the body and an upper portion of the nozzle is spaced from said body to form a gap so that the front end can expand into the gap to lock the body to the nozzle when the sealing disc is positioned at the front end.

14. A disposable capsule according to claim 13, wherein the disc is self-sealing so that a hypodermic needle can pass through said disc, so that the fluid to be injected can be placed within the body without affecting the sealing function of the disc when the needle is removed.

15. The disposable capsule according to claim 13, wherein once the capsule is fully mounted in a sterile environment, it is introduced into an individual package similar to that utilized for disposable syringes, which allows it to undergo a heat-free sterilization process by gases and which when tampered, is capable of leaving a definite sign of this tampering.

16. A disposable capsule, for needleless hypodermic injection device, comprising:
   a hollow body having a front end closed by a top wall, and a rear end that is closed by a bottom wall that is attached to the body by an outwardly extending flange having a smaller thickness than a remaining portion of the bottom wall, said top wall is attached to the body and has a center portion having a smaller thickness than the remaining portion of the top wall so that it can be easily ruptured, and said body is connectable to said hypodermic injection device so that a piston in the injection device can engage the bottom wall and detach said flange from the body;
   a nozzle, attached to the front end of the body, having a minute front orifice through which a liquid to be injected can be expelled in the form of a jet; and
   a sealing disc positioned within the body at the rear end so as to prevent a liquid within the body from leaking out the rear end, said disc is movable from a first position at the rear end of the body to a second position at the front end of the body so that the top wall can be ruptured and the liquid to be injected expelled out said orifice, said disc moves when said piston detaches the flange and moves the bottom wall toward the front end.

* * * * *